United States Patent
Paul, Jr.

(10) Patent No.: US 7,187,977 B2
(45) Date of Patent: Mar. 6, 2007

(54) TRANSCUTANEOUS ELECTRICAL NERVE STIMULATION DEVICE AND METHOD USING MICROCURRENT

(75) Inventor: Edward L. Paul, Jr., Wrightsville Beach, NC (US)

(73) Assignee: Atlantic Medical, Inc., Wrightsville Beach, NC (US)

( * ) Notice: Subject to any disclaimer, the term of this patent is extended or adjusted under 35 U.S.C. 154(b) by 491 days.

(21) Appl. No.: 10/457,857

(22) Filed: Jun. 10, 2003

(65) Prior Publication Data

US 2003/0233137 A1    Dec. 18, 2003

Related U.S. Application Data

(60) Provisional application No. 60/388,577, filed on Jun. 13, 2002.

(51) Int. Cl.
*A61N 1/00* (2006.01)
(52) U.S. Cl. ............... 607/48; 607/69; 607/71
(58) Field of Classification Search ........... 607/48, 607/68, 69, 71, 76
See application file for complete search history.

(56) References Cited

U.S. PATENT DOCUMENTS

| | | | | |
|---|---|---|---|---|
| 4,019,510 A * | 4/1977 | Ellis | | 604/20 |
| 4,712,558 A | 12/1987 | Kidd et al. | | 128/421 |
| 4,989,605 A * | 2/1991 | Rossen | | 607/46 |
| 5,314,423 A | 5/1994 | Seney | | 606/20 |
| 5,324,317 A | 6/1994 | Reiss | | 607/67 |
| 5,447,526 A | 9/1995 | Karsdon | | 607/39 |
| 5,522,864 A | 6/1996 | Wallace et al. | | 607/53 |
| 5,549,656 A | 8/1996 | Reiss | | 607/48 |
| 5,571,150 A | 11/1996 | Wernicke et al. | | 607/72 |
| 5,611,350 A | 3/1997 | John | | 128/731 |
| 5,702,428 A | 12/1997 | Tippey et al. | | 607/41 |
| 5,713,940 A | 2/1998 | Karsdon | | 607/39 |
| 5,800,458 A | 9/1998 | Wingrove | | 607/2 |
| RE35,987 E | 12/1998 | Harris et al. | | 607/63 |
| 5,851,223 A | 12/1998 | Liss et al. | | 607/46 |
| 5,935,156 A * | 8/1999 | Chandler et al. | | 607/66 |
| 5,964,789 A | 10/1999 | Karsdon | | 607/39 |
| 6,035,236 A | 3/2000 | Jarding et al. | | 607/53 |
| 6,066,163 A | 5/2000 | John | | 607/45 |
| 6,219,578 B1 | 4/2001 | Collins et al. | | 607/2 |
| 6,275,735 B1 | 8/2001 | Jarding et al. | | 607/53 |
| 6,393,319 B1 | 5/2002 | Bock et al. | | 607/2 |
| 6,445,955 B1 | 9/2002 | Michelson et al. | | 607/46 |

OTHER PUBLICATIONS

"Clinical Orthopaedics and Related Research"—Cheng et al.
"Can ELF Help Your Patients?"—Thomas W.Wing, D.C., N.D.
Letter from Dr. Joel S. Rossen to Dr. Edward L. Paul, inventor of the present invention.
U.S. FDA Document relating to Dr. Joel S. Rossen's invention described in the letter.

* cited by examiner

Primary Examiner—Robert E. Pezzuto
Assistant Examiner—Brian T. Gedeon
(74) Attorney, Agent, or Firm—Gardner Groff Santos & Greenwald, P.C.

(57) ABSTRACT

A transcutaneous electrical nerve stimulation device and method using a microcurrent with a carrier signal and a square wave form for promoting cell repair and/or healing. It has been found that applying particular wave forms of direct current with a carrier wave signal with specified intervals promotes cell healing especially in treatment of macular degeneration. This method and nerve stimulation device is packaged to require no input from a user and a user must only apply the electrodes to the correct part of the body and start the preprogrammed sequence of electrical currents. The method involves applying bursts of direct current at higher frequencies for shorter periods of time followed by lower frequency bursts of electrical current for longer periods of time.

9 Claims, 6 Drawing Sheets

FIG. 1
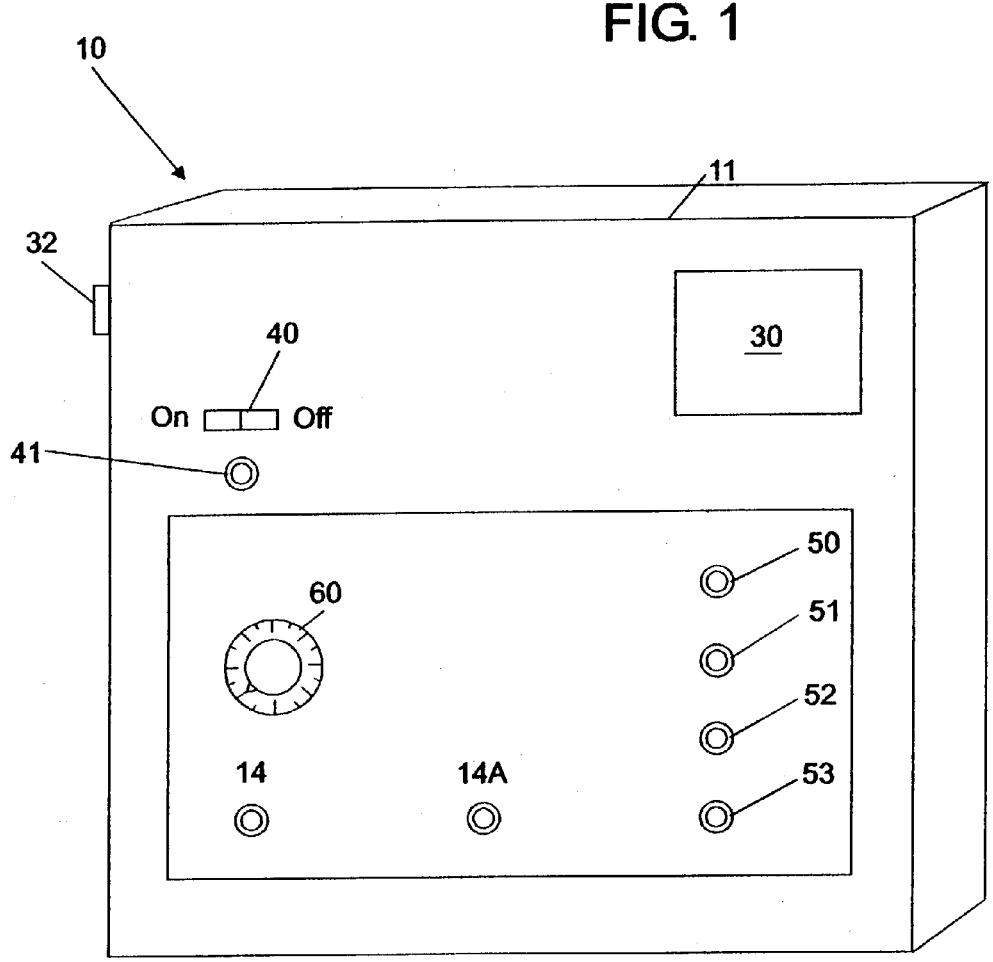
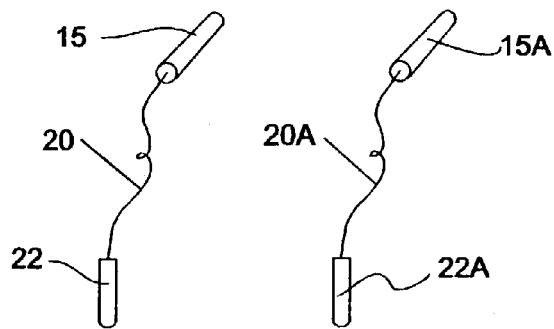

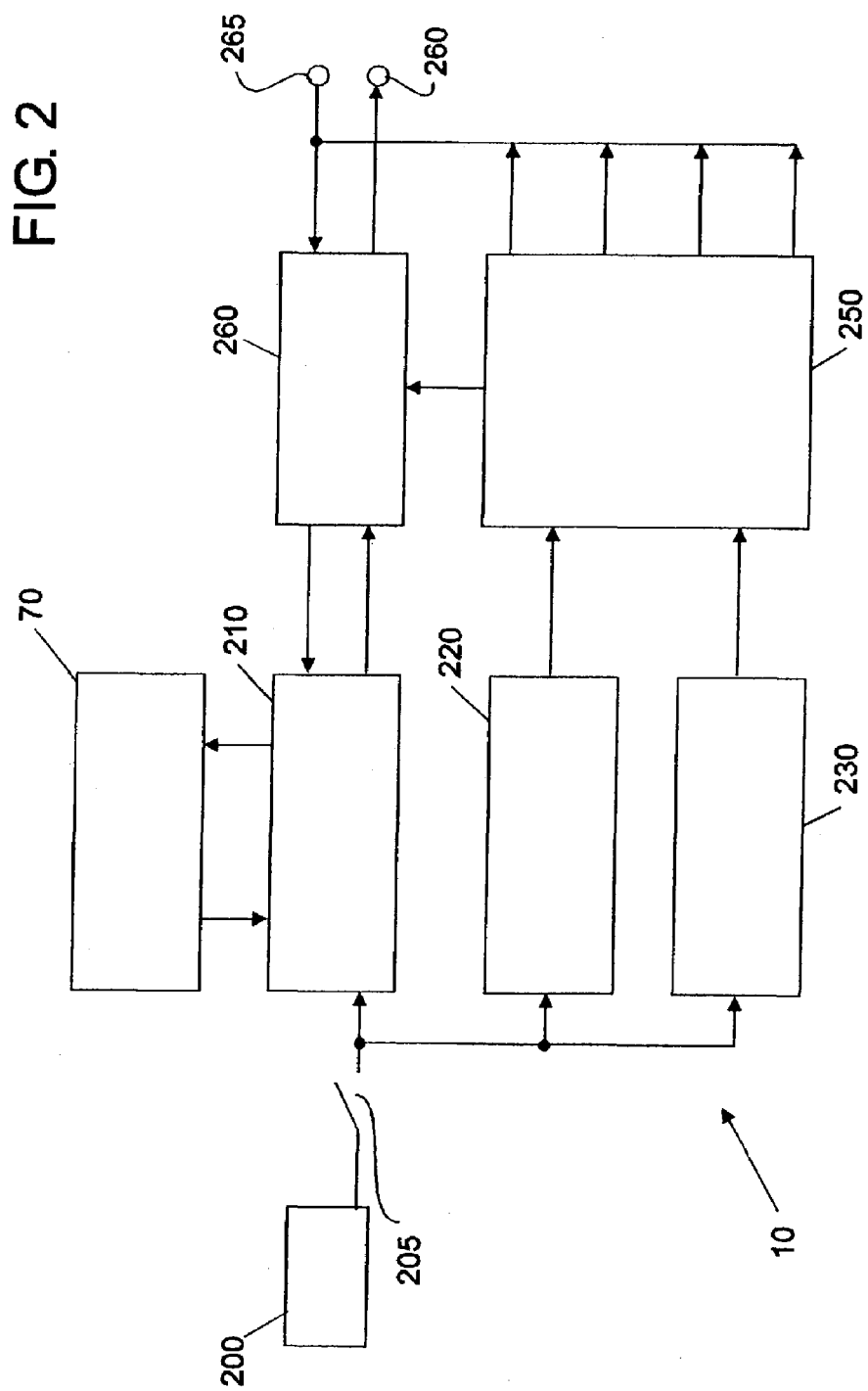

| FIG. 3A | FIG. 3B |

TRANSCUTANEOUS ELECTRICAL NERVE STIMULATION DEVICE AND METHOD USING MICROCURRENT

RELATED APPLICATION

This application claims the benefit of U.S. provisional application No. 60/388,577 accorded a filing date of 13 Jun. 2002.

FIELD OF THE INVENTION

This invention relates generally to a transcutaneous electrical nerve stimulation (TENS) apparatus for use for therapeutic purposes. This device proposes using electrical current in the microamp range (less than one milliamp) for specific wave forms and carrier waves. The treatment duration is of a definite length and sequence with proposed automatic controls. The wave form, the current, and the duration of treatment are all designed to maximize therapeutic benefits. Microcurrent is defined as current below one milliamp. For pain treatment, it is believed that the microcurrent blocks neural transmission of pain signals and stimulates release of endorphins known to be naturally occurring pain relieving chemicals. The combination of the blocking of the pain signals and release of the endorphins provides for relief of both chronic and acute pain. It is also believed that microcurrent stimulation can promote healing or cell repair. The exact mechanism of promotion of cell repair is unknown. However, it is believed that this can be done by increasing blood vessel permeability, increasing adenosine triphosphate levels, or restoring cellular electrical balances by changing electric potentials across cell membranes.

BACKGROUND OF THE INVENTION

One TENS device is described in the Rossen U.S. Pat. No. 4,989,605. It is believed this device has been sold on the market by the trade name "MicroStim". The Rossen '605 patent discloses a microcurrent TENS unit that uses a unique wave form. It is proposed the current is from 250 microamps up to about 900 microamps with a peak current of six milliamps. The current is applied through a pair of electrodes in the form of high-frequency monophasic bursts of a direct current with a carrier signal from around 10,000 Hz to 19,000 Hz. The signal is modulated at a relatively lower frequency (0.3 Hz up to 10,000 Hz). These modulated carrier signals are from about 0.05 seconds to 10 seconds in duration with above one second being the preferred duration. The electrodes are reversed as simulating a biphasic form yet the character is a monophasic DC signal. The Rossen patent is for palliative pain treatment only.

The Wallace U.S. Pat. No. 5,522,864 proposes that macular degeneration or other ocular pathology may be treated by placing a positive electrode of a direct microcurrent source in contact with the closed eyelid of the subject and placing a negative electrode away from the eye of the subject, preferably on the neck of the subject. These electrodes apply a constant direct current of 200 microamps for approximately 10 minutes. It is proposed that this device can be portable and battery powered, hence allowing a subject undergoing the treatment to ambulate during the treatment. The Wallace patent proposes using microcurrent to treat macular degeneration but does not disclose the mechanism by which positive results are obtained.

The Jarding et al. U.S. Pat. No. 6,275,735 proposes digital control of the modulation frequency of the microcurrent signal. The modulation frequency is controlled by a digital data word. A controller is coupled to a digital analog converter and supplies the digital analog converter with digital data words to generate an electrical signal for the microcurrent stimulation therapy. It is believed that this form of microcurrent therapy may be particularly useful in macular degeneration. More specifically, the Jarding patent proposes that adenosine triphosphate levels in cells can be affected by appropriate electrical stimulation. Jarding proposes that electrical stimulation to the cells increases blood vessel permeability, increasing ATP levels and increasing protein synthesis. Therefore, Jarding concludes that microcurrent stimulation can help rejuvenate cells in the retina to slow or stop degeneration of the eye due to age-related macular degeneration. Therefore, Jarding proposes a computer controlled electrical stimulation to maximize therapeutic benefits by varying the types of wave forms and frequency ranges used in the therapy.

Another problem present in the use of TENS units for therapeutic or palliative effect is patient compliance. Wingrove U.S. Pat. No. 5,800,458 proposes a compliance monitor to determine if the patient is using the TENS unit in accordance with instructions or prescriptions. Another problem with conventional TENS units is they can be bulky or difficult to control. This can especially apply to individuals who have some disability or who are in acute pain. Michelson et al. U.S. Pat. No. 6,445,955 proposes a miniature wireless TENS unit. A remote controller sends transmission signals to a receiver within an electronic module with the TENS unit allowing the patient to program specific units in a specific way. The TENS unit itself may be incorporated within a bandage or electrode package and worn directly on the patient's body.

It has also been proposed, at least in a research context, that the wrong current levels used in transcutaneous electrical nerve stimulation can actually reduce ATP levels and may cause more harm than good. Research by Ngok Chen would demonstrate, at least in rats, that current levels in the microamp range tended to increase ATP concentration in cells while currents in the milliamp range tended to lower ATP concentration in cells. (See Chen, *The Effects of Electrical Current on ATP Generation, Protein Synthesis, and Membrane Transport in Rat Skin*, Clinical Orthopedics Research, 171, November–December 1982, pp. 264–271) It has also been suggested by Thomas W. Wing, D.C., N.D. that direct current employing a carrier wave with a low frequency is very helpful triggering the repair process in muscles. Wing suggested only very low levels of stimulation are required if the effect of the direct electrical current at a low frequency was the triggering of the body's natural repair cycle. Wing suggests that low frequencies of 0.1 to 0.3 Hz produce lasting therapeutic effects, but pain relief is more rapid at higher frequencies in the 10 to 100 Hz range. Thomas W. Wing, D. C., N. D. *Chiropractic Economics*, March/April 1987. The Food and Drug Administration has approved the use of TENS units for symptomatic relief of chronic pain and to manage post surgical traumatic pain problems. The therapeutic use to treat macular degeneration proposed by Wallace et al in the '864 patent is an off label use of a TENS device, that is, this use is not approved by the FDA. However, in order to obtain FDA approval for a TENS unit for treatment of degenerative diseases such as macular eye disease, tissue repair, and cell regeneration, require proof of effectiveness. Proof is obtained through double blind, randomized, and multi-site clinical trials. It is believed such trials are underway to document effectiveness of a TENS unit for the treatment of age related macular degeneration.

The use of a TENS unit both for palliative and therapeutic treatment is well established, but the precise mechanism by which it operates is not fully understood. This means that even small differences in how an electrical current is applied can have unpredictably large changes in the therapeutic outcome. That is to say, a current of 200 microamps might be therapeutic, while a current of 400 microamps might actually be harmful. By the same token, such factors as whether the current is applied in a wave form, whether the polarity of the current alternates, and the like all can have important impacts in either the palliative or the therapeutic effect. Consequently, the optimal use of a TENS unit for either palliative or therapeutic effects proceeds more by experimentation than by theoretical design. That is to say, there is no theory by which one can design an ideal or maximally beneficial treatment modality for a particular TENS unit, then experiment to confirm the correctness of the program. Theory may point one in the right direction, but then an inventor must use intuition, clinical judgement, and experimentation to arrive at a therapeutic program giving maximum benefits.

Despite this earlier work there is still need for a TENS unit and treatment method to meet specific goals and needs. First, in the correct method, the TENS units must always operate in a current range that maximizes the benefits of the electrical nerve stimulation. Second, the duration and frequency of the electrical stimulation must be controlled to maximize the benefits. Third, control of the TENS unit should be designed to maximize compliance of a patient. Therefore, it is an object of the current invention to provide a fully automated and computer controlled microcurrent stimulation device. It is a further object of the invention to administer a therapeutic electrical current in the microamp range, always less than one milliamp. It is a further object of the invention that the current be administered in a square wave form in a sequential pattern of specific electrical bursts with frequencies between 0.1 Hz and 300 Hz. It is a further object of the invention to control the duration of the application of each electrical current bursts with the specified frequency for a specific period of time and sequence the application of the current controlled by an internal control to minimize patient compliance issues and to maximize benefit. It is a further object of this invention to periodically reverse the polarity of the current flow at specific intervals. It is a further object of this invention to give visual and audible cues as to the treatment being administered at any given time. It is an object of the invention to provide minimal controls or requirements for patient input or control. It is a further object of the invention that the TENS unit will be ergonomically designed and easily used by those with physical disabilities.

SUMMARY OF THE INVENTION

The present consists of a microcurrent stimulator ordinarily housed in a rigid casing. Inside that casing are controls to produce and apply a microcurrent transcutaneous electrical nerve stimulation. The controls are preprogrammed to provide a therapeutic level of electrocurrent in the microamperage range in a square wave form with a specific sequential pattern of specific electrical bursts with specific frequencies and to reverse the current flow at specific time intervals by reversing the electrode polarity. The application of the specific electrical carrier frequencies and microamperage current is controlled for duration and is sequenced by the control. Ordinarily, there will be both visual and audible cues given to a user by the microcurrent stimulator. The multiple frequencies begin with a higher frequency and work down to a lower frequency.

This microcurrent stimulation unit has minimal settings adjustments or controls for patient use. It is believed the microcurrent stimulation device should be preset by a physician or other clinician at specific durations and frequencies to maximize therapeutic benefit. A specific carrier frequency would be used in the range of 10,000 Hz to 15,000 Hz. The current will be delivered in the microamp range less than one milliamp. A square wave form will be employed. Specific electrical bursts with specific frequencies, no more than 300 Hz and no less than 0.1 Hz, will be employed. A typical pattern of bursts would be a 292 Hz frequency applied for 60 seconds, a 30 Hz frequency applied for 120 seconds, a 9.1 Hz frequency applied for 180 seconds, and a 0.3 Hz applied for 360 seconds. The electrode polarity will be reversed every two seconds. A therapeutic program will ordinarily be in the range of 12 minutes of duration according to a pre-programmed, pre-set treatment sequence with controlled current levels and wave forms to have the greatest therapeutic value. As the therapeutic program is being administered, the unit will have visual and audible waves of signaling to a user the progress of the therapy program. The unit will have ways of alerting a user to malfunctions or to low-battery. Other features and advantages of the invention will become apparent in the Detailed Description of the Drawings, which follow.

BRIEF DESCRIPTION OF THE DRAWINGS

FIG. 1 shows the microcurrent stimulation device.

FIG. 2 is a block diagram of the essential components of the microcurrent stimulation device.

DETAILED DESCRIPTION OF THE DRAWINGS

Figures 3, 3A:
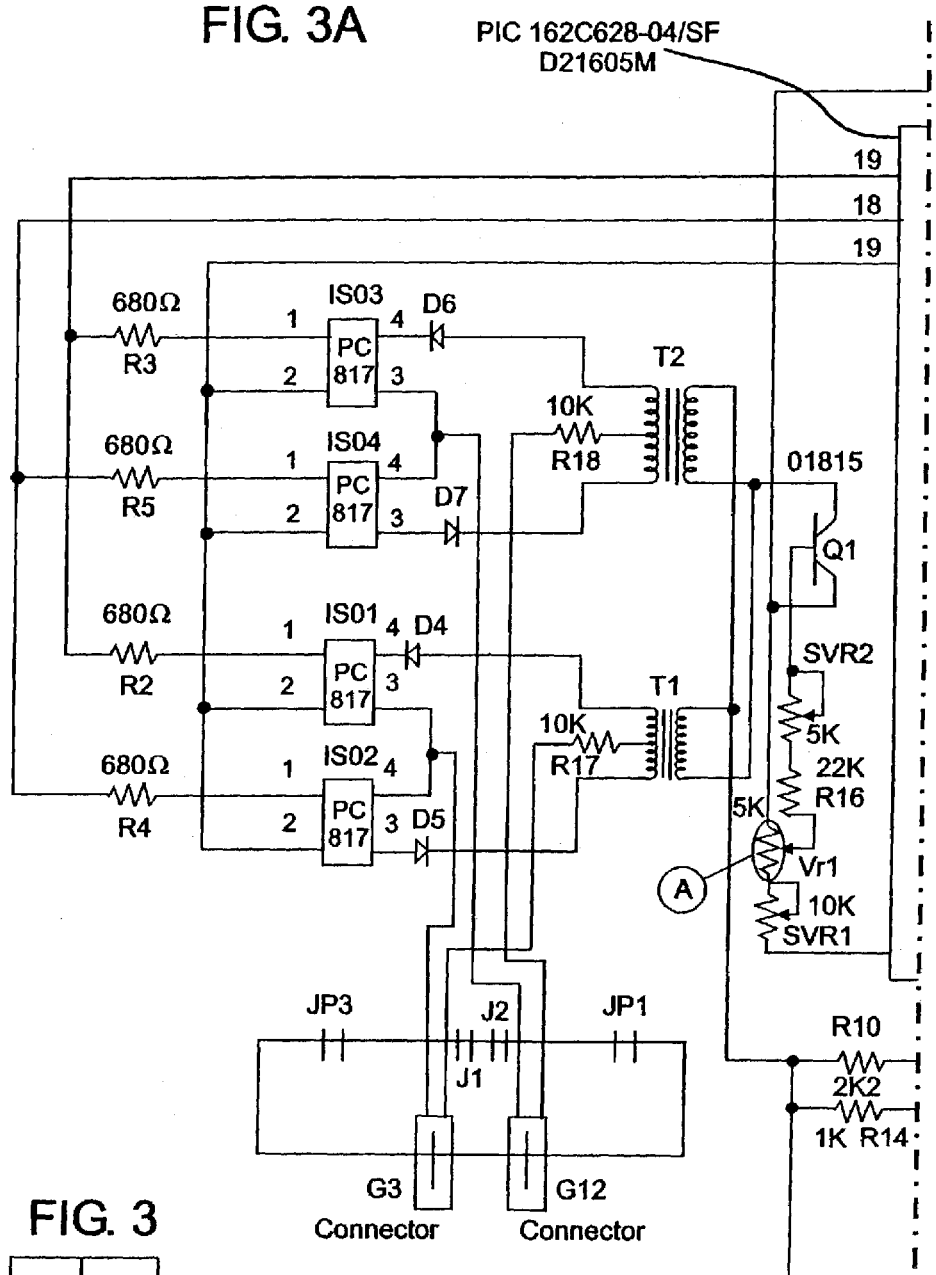
FIG. 3 is a circuit diagram of an embodiment of the current invention.
Figure 3B:
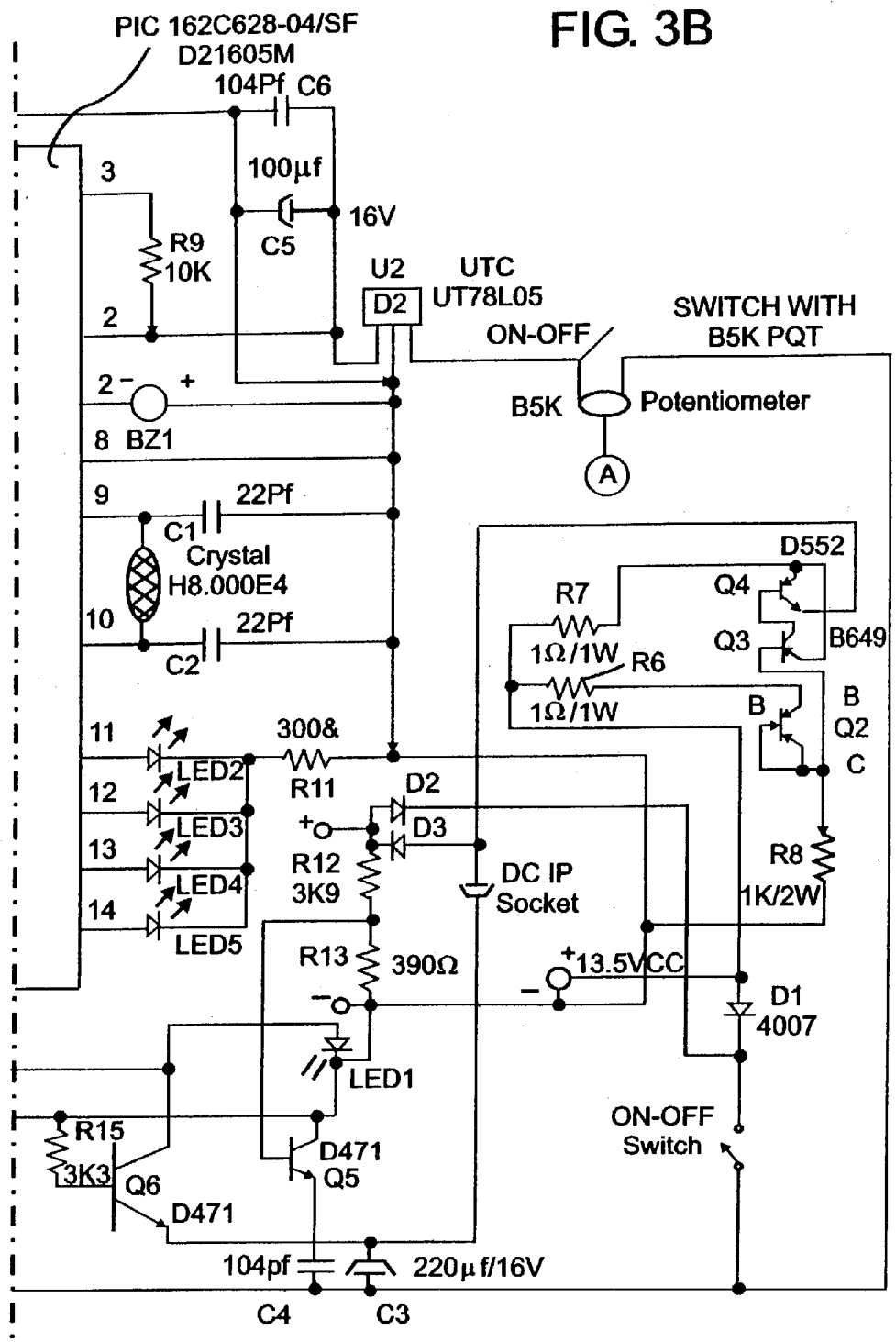
Figure 4:
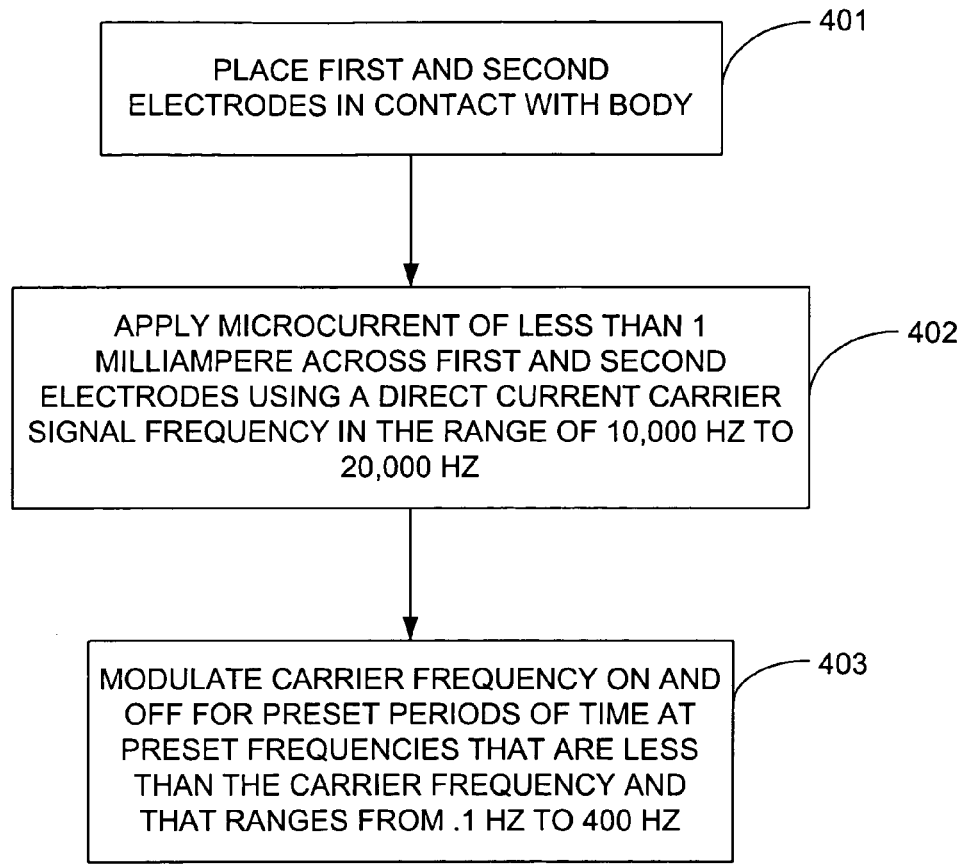
FIG. 4 illustrates a flowchart that demonstrates the method of the invention of applying a microcurrent across the electrodes using a direct current carrier signal having a frequency between 10,000 Hz and 20,000 Hz, which is modulated on and off at preset frequencies for preset periods of time in a sequence in which the preset frequencies sequentially decrease and the preset time periods sequentially increase.
Figure 5:
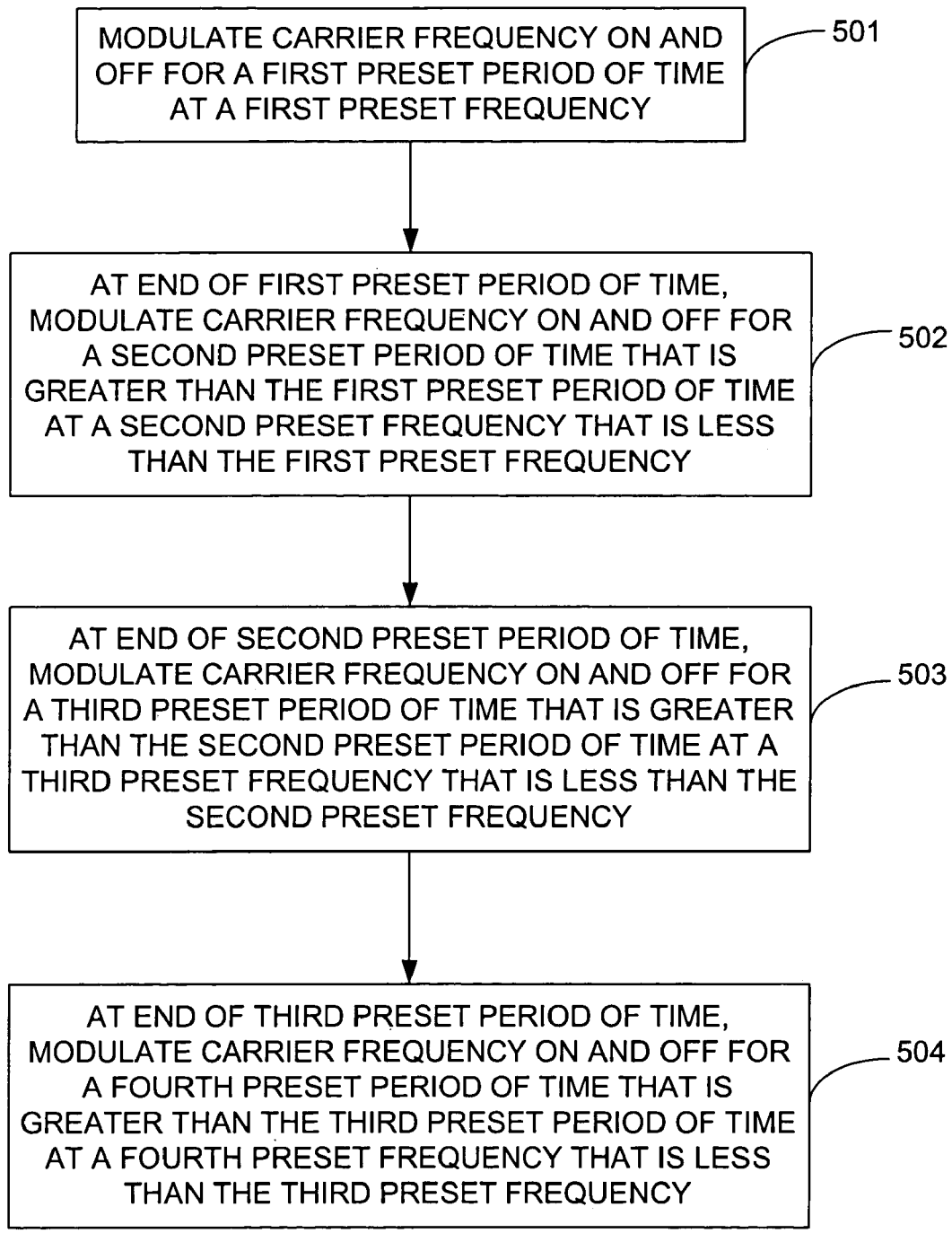
FIG. 5 illustrates a flowchart that demonstrates the method of the invention in accordance with an exemplary embodiment in which the carrier signal is modulated on and off at first, second and third preset frequencies over first, second and third preset time periods, wherein the first, second and third preset frequencies sequentially decrease and the first, second and third time periods sequentially increase.

FIG. 1 shows the microcurrent stimulation device (10). Ordinarily, there is a box (11) with various components and controls. Connected to the box (11) are at least two electrodes (22) and (22A) that connect to the box (11) as part of the microcurrent nerve stimulation device (10). If the polarity of the current is reversed as part of a treatment method, then more than two electrodes may be employed. Electrodes (22) and (22A) connect by means of wires (20) and (20A) and probes (15) and (15A) to electrode jacks (14) and (14A) in the front of the box (11). Electrodes (22) and (22A) will be applied to a user completing an electrical circuit which allows a microcurrent to pass from one electrode through the body of the user to the other electrode to complete the circuit. Contained within the box (11) are control circuitry and microprocessors which may be programmed to provide particular types of current in particular wave forms, as will be explained later in the application. On the front of the box (11) is a turn dial control knob (60) that controls the amount of current passing through the electrodes (22) and (22A) and from jacks (14) to (14A) or vice versa. There is a slide on/off switch (40) and an indicator light (41) that indicates when the microcurrent nerve stimulation device is operating. Ordinarily, batteries will supply the power, which are contained in the battery unit (30) on the front of the box (11). Alternately a direct current to power the microcurrent nerve stimulation device (10) may be supplied through the power jack (32), shown on the side of the box (11). When the indicator (41) is dim or not on, it means that the batteries (30) are low and need replacing or that no power is being supplied through the power jack (32). Disposed on the right-hand side of the box (11), from the viewer's perspective, are four program indicator lights (50, 51, 52, 53).

To use the microcurrent nerve stimulation device (10), the user will ordinarily apply the electrodes (22) and (22A) to a prescribed place as determined by a health care provider. The leads (15) and (15A) will be connected to the inputjacks (14) and (14A). The on/off switch (40) will turn the device on and the control knob (60) will be adjusted by a user to the appropriate amount of current. Typically, a user will turn the control knob (60) to a level of current where a mild tingle indicating electrical current will be felt, then the control knob (60) will be adjusted downward to reduce the amount of current to where the current is no longer a perceptible tingle to a user. The microcurrent nerve stimulation device (10) will then begin to follow a pre-programmed sequence in which current will be provided with a particular frequency and wave form. In the preferred program, current will be provided in a square wave form at a frequency of 292 Hz for 60 seconds. During those 60 seconds the program indicator light (50) is lit, which advises the user that the program is underway. When the current applied at 292 Hz for 60 seconds stops, an audible tone will sound and the next step in the therapy program will begin. Here, program indicator light (51) will light, current will be provided at 30 Hz for 120 seconds. At the conclusion of this step in the therapy program, a tone will sound again. The program indicator light (51) will dim and program indicator light (52) will light. This indicates that current will be provided at 9.1 Hz for 180 seconds. A third tone will sound indicating that step in the therapy program is over. Program indicator light (52) will dim and program indicator light (53) will light up. Current will be provided for 0.3 Hz for 360 seconds. At the conclusion of this therapy, a tone will again sound and the therapy program will end and the microcurrent nerve stimulation device (10) will stop the therapy program. During the therapy program the polarity of the electrodes (22) and (22A) will reverse every two seconds. At this point, a user will remove the electrodes (22) and (22A), turn the on/off switch (40) to off, and the microcurrent nerve stimulation device (10) is ready to begin another treatment program or maybe stored until required for further use.

FIG. 2 shows a block diagram of the electrical components for an embodiment of the microcurrent stimulation device (10) as seen in FIG. 1. A more complete description of electrical components of one embodiment is shown in the circuit diagram in FIG. 3. There is a direct current power supply (200). In a commercial embodiment, this could be a nine-volt battery or household current adopter to supply nine volts to a connection or jack provided on the microcurrent stimulation device (10) as shown in FIG. 1. Current flows through an on/off switch (205) to voltage convertor (210) to a regulator (220) and to a oscillator (230). Current flows from the regulator (220) and oscillator (230) to a frequency divider (250). A constant current source (260) receives current from the frequency divider (250) and from the voltage convertor (210) then passes from the constant current source to a first electrode (260). A circuit is completed from the first electrode (260) through the patient (not shown) to a second electrode (265). Current returns to the constant current source (260) to the voltage convertor (210) through an amplitude control (70) and then to the power source (200) to complete the circuit.

FIG. 3 is a circuit diagram of a commercial embodiment of a microcurrent stimulation device (10). Standard symbols and terminology are used in labeling the circuit diagram shown in FIG. 3. For simplicity of the diagram, the potentiometer labeled "VR1" is shown in two places on the circuit diagram, but in the actual circuit there is only one VR1 potentiometer. This is indicated by the letter "A" with a circle around it and the arrow. This points to the same part. It will be understood that there is not two potentiometers, but only one from 5K to 85K resistance. A materials list is given below. The standard devices in FIG. 3 are labeled in accordance with the materials list. Controls are provided by five computer chips. Four chips are a high-density photocoupler chip. One chip that has been found to work in practice is manufactured by the Sharp Company and assigned product #PC817X. One chip is a programmable read only memory chip. One chip that has been found to work in practice is manufactured by Microchip. It is a 28 Pin, 8 Bit Micro Controller Chip and is assigned part #PIC16C628-04. This chip is equipped with timers, data memory, and other features required to produce and control appropriate microcurrent output and polarity. It will be appreciated by one of skill in the art that such standard things as diodes, resistors, capacitors, transformers, transistor switches and the like, which appear on the circuit diagram, can be varied without departing from the essentials of the invention, which is to produce microcurrents with specified wave forms and carrier frequencies timed in a way to maximize the benefit and to induce patient compliance.

MATERIALS LIST

RESISTORS $R_1$ - JUMPER WIRE (no resistor)
$R_2$ - 680Ω
$R_3$ - 680Ω
$R_4$ - 680Ω
$R_5$ - 680Ω
$R_6$ - 1Ω/1 W
$R_7$ - 1Ω/1 W
$R_8$ - 1K/2 W
$R_9$ - 10 KΩ
$R_{10}$ - 2K2
$R_{11}$ - 330Ω
$R_{12}$ - 3K9
$R_{13}$ - 390Ω
$R_{14}$ - 1 KΩ
$R_{15}$ - 3K3
$R_{16}$ - 22 kΩ
$R_{17}$ - 10 kΩ
$R_{18}$ - 10 kΩ

-continued

MATERIALS LIST

DIODES $D_1$ - 4007
$D_2$ - 4007
$D_3$ - 4007
$D_4$ - 4148
$D_5$ - 4148
$D_6$ - 4148
$D_7$ - 4148

BUZZER

BZ1 - 080
ON-OFF Switch

CAPACITORS $C_1$ - 22pf
$C_2$ - 22pf
$C_3$ - 220 µf/16 v
$C_4$ - 104pf
$C_5$ - 100 µf/16 v
$C_6$ - 104pf

TRANSISTORS $Q_1$ - C1815
$Q_2$ - B649
$Q_3$ - B649
$Q_4$ - DB82
$Q_5$ - D471
$Q_6$ - D471

INTEGRATED CIRCUIT CHIPS

IS01 - PC817
IS02 - PC817
IS03 - PC817
IS04 - PC817
PIC 16C628 - 04/SF
D21605M
UT78L05

LEDS $LED_1$ - Dipole LED
$LED_2$ - Green LED 5 mm
$LED_3$ - Green LED 5 mm
$LED_4$ - Green LED 5 mm
$LED_5$ - Green LED 5 mm

CRYSTAL OSCILLATOR -

H8.000E4
2 TRANSFORMERS

POT (VRI) 5k (85k)
PRESET VARIABLE RESISTANCE

SVR1 - 103(10k)
SVR2 - 503(50k)
ON-OFF Switch

The treatment protocol employing the embodiment described in FIGS. 1, 2, and 3 can be used specifically to treat macular degeneration of an eye. It is believed this operates, at least in part, by stimulating cell activities producing an increased ATP concentration. In this specific treatment protocol, a patient will first prepare the appropriate skin area by careful washing and drying to remove skin oils, cosmetics, or other foreign materials from the skin surface. A patient will connect a pair of electrode pads (not shown) to the electrode input jacks (14) and (14A) on the, microcurrent nerve stimulation device (10). The electrode pads (not shown) ordinarily have a sticky surface so that they will adhere to the skin. An electrode pad is placed on the back of each hand. An electrode pad is placed on the closed eyelid of each eye. If the microcurrent nerve stimulation device (10) is not already on, the control switch (40) will be turned to on and the intensity knob will be adjusted to intensity to a preset figure on the intensity knob, usually '8'. Then the knob will be individually adjusted by a user to that user's comfort level according to a set of instructions provided with the unit. Only current in a predetermined microamperage is applied.

The microcurrent nerve stimulation device (10) is programmed to deliver 12 minutes of treatment for treatment of macular degeneration. The microcurrent nerve stimulation device (10) is also programmed to audibly notify a user as the treatment proceeds at each stage of the treatment. For treatment of macular degeneration, there will be a first current at a frequency of 292 Hz with a square wave form for 60 seconds. The amperage output will be no more than 999 microamps. When the 60-second application at 292 Hz is complete, a first beep will sound. The microcurrent nerve stimulation device (10) will automatically start a second microcurrent stimulation at 30 Hz for 120 seconds. Ordinarily, the amount of amperage will not be adjusted and will remain constant throughout the treatment. When the 120-second application is complete, a second audible tone will sound and the third period of microcurrent stimulation will begin. Again, it will be controlled automatically by the microcurrent nerve stimulation device (10) to apply 9.1 Hz frequency at 180 seconds. A third tone will sound and the microcurrent nerve stimulation device (10) will start a fourth sequence at a frequency of 0.3 Hz for 360 seconds. At the completion of this, a fourth tone will sound, which will also notify the user that the treatment is complete. During the treatment the microcurrent nerve stimulation device (10) will reverse the polarity of the electrodes every two seconds. If a user experiences discomfort during application of the treatment, the intensity knob (60) will be adjusted downward to a position where the user will no longer experience discomfort. The treatment is ordinarily administered twice a day—once in the morning and once in the evening. It has been found in practice that stimulating with a square wave form for the intervals and frequencies described above is an effective treatment for macular degeneration.

Case Histories

Case history #1 is an eighty-year-old white female with a five-year history of age-related macular degeneration. The diagnosis was confirmed by a board certified retinal specialist ophthalmologist. The patient's medical history for her eyes indicated she was pseudophakic in both eyes with cataract surgery seven years prior to treatment. The chief complaint was decreased central vision acuity progressing to the point of loss of driving privilege. The remainder of the medical history was unremarkable and the patient's other medications were unremarkable.

Entrance visual acuity on her initial examination was 20/80 OD and 20/160 OS. A computerized Macular Mapping Test (MMT) was performed showing a central scotoma in the right eye with an adjusted score of 70.50 and a central scotoma in the left eye with an adjusted score of 69.00. Pupils are reactive and equal and her external and internal eye exam were within normal limits with the exception of IOL's OU and age-related macular degeneration. Based upon the confirmed diagnosis age-related macular degeneration, the patient was started on microcurrent stimulation therapy. Her treatment protocol consisted of two, twelve minute sessions each day. Each session consisted of 500–800 microamps of current at four separate electrical frequencies. 292 Hz for 60 seconds, 30 Hz for 120 seconds, 9.1 Hz for 180 seconds, and 0.3 Hz for 360 seconds.

After four days of microcurrent stimulation therapy, the patient reported an improvement in her subjective ability to see. Visual acuity was reevaluated and found to have improved to 20/60 OD and 20/100 OS. MMT was repeated and showed a decrease in the size of the central scotomas in both eyes with adjusted scores of 96.50 OD and 93.00 OS. The therapy was continued with two, twelve minute sessions each day and at six weeks the patient was evaluated by her original retinal specialist. He confirmed that her visions had indeed stabilized and improved.

Case history #2 is a 55 year old professional white male. The patients had a two-year history of age-related macular degeneration with the diagnosis confirmed by three separate ophthalmologists. He was on medical disability from his employment because of visual disability. The medical history for the patient was otherwise unremarkable and no other eye pathology was reported.

Entrance visual acuity measured 20/40 OD and 20/50 OS. Amsler grid testing reveals metamorphopsia in both eyes. Pupils are reactive and equal. The fundus exam reveals drusen in the posterior pole of both eyes which is indicative of macular degeneration. The rest of the ocular exam is within normal limits with no other ocular pathology present. Based upon the confirmed diagnosis age-related macular degeneration, the patient was started on microcurrent stimulation therapy. His treatment protocol consisted of two, twelve minute sessions each day. Each session consisted of 500–800 microamps of current at four separate electrical frequencies. 292 Hz for 60 seconds, 30 Hz for 120 seconds, 9.1 Hz for 180 seconds, and 0.3 Hz for 360 seconds.

After five days, the patient was reevaluated. Visual acuity had improved to 20/25 OD and 20/30 OS. There had been a subjective improvement in the patient's ability to read comfortably and without visual stress. Amsler grid testing revealed persistent metamorphopsia, however it was less pronounced. The patient continued with two, twelve minute therapy sessions each day and was able to resume work. Upon reexamination by his original ophthalmologist, he was told that his macular degeneration had actually reversed and his vision had improved.

I claim:

1. A method for applying microcurrent electrical stimulation to a body, the method comprising the steps of:
    (a) attaching at least a first electrode in proximity to a specific body part and attaching at least a second electrode on the body at a point away from said specific body part;
    (b) applying a microcurrent across said first and said second electrode wherein said microcurrent is greater than 900 microampere and less than 1 millampere;
    (c) using a direct current carrier signal for said microcurrent, said carrier signal frequency from 10,000 Hz up to 20,000 Hz; and
    (d) modulating said carrier signal on and off at at least first, second and third preset frequencies during at least first, second and third preset time periods, respectively, each of said preset frequencies being lower than said carrier signal frequency, the first preset frequency being higher than the second preset frequency, the second preset frequency being higher than the third preset frequency, the third preset time period being greater than the second preset time period, the second preset time period being greater than the first preset time period, the second preset time period beginning when said first preset time period ends, said third preset time period beginning when said second preset time period ends.

2. The method of claim 1 wherein said step of modulating said carrier signal on and off further includes applying said preset frequencies in a square wave form.

3. The method of claim 2, wherein the first preset frequency is higher than 200 Hz but lower than or equal to 300 Hz, and wherein said first preset time period is from one second up to 120 seconds.

4. The method of claim 3 wherein said second preset frequency is higher than 10 Hz but lower than or equal to 200 Hz, and wherein said second preset time period is from one second up to 240 seconds.

5. The method of claim 4 wherein said third preset frequency is higher than 1 Hz but lower than or equal to 10 Hz, and wherein said third preset time period is from 10 seconds up to 800 seconds.

6. The method of claim 5 further includes steps of modulating said carrier signal on and off at at least a fourth preset frequency for at least a fourth preset time period, wherein said fourth preset frequency is higher than 0.1 Hz but lower than or equal to 1 Hz, and wherein said fourth preset time period is from 10 seconds up to 500 seconds.

7. The method of claim 6 wherein said first preset frequency is approximately 292 Hz, said second preset frequency is approximately 30 Hz, said third preset frequency is approximately 9.1 Hz, and said fourth preset frequency is approximately 0.3 Hz.

8. The method of claim 7 wherein further includes said step of reversing the polarity of said microcurrent at an interval from one to three seconds.

9. The method of claim 8 wherein said step of reversing the polarity of said microcurrent occurs at an interval of two seconds.

* * * * *